United States Patent [19]
Kress et al.

[11] Patent Number: 6,084,371
[45] Date of Patent: Jul. 4, 2000

[54] APPARATUS AND METHODS FOR A HUMAN DE-AMPLIFIER SYSTEM

[75] Inventors: Reid L. Kress, Oak Ridge; John F. Jansen, Knoxville, both of Tenn.

[73] Assignee: Lockheed Martin Energy Research Corporation, Oak Ridge, Tenn.

[21] Appl. No.: 09/253,186

[22] Filed: Feb. 19, 1999

[51] Int. Cl.$^7$ ...................................................... B25J 7/00

[52] U.S. Cl. .............. 318/566; 318/568.19; 318/568.21; 318/568.22; 318/621

[58] Field of Search ............................... 318/566, 568.11, 318/568.16, 568.19, 568.21, 568.22, 621, 623, 632; 294/86.4, 99.1, 99.2, 100, 103.1, 907; 901/30, 31, 36, 38, 39

[56] References Cited

U.S. PATENT DOCUMENTS

| | | | |
|---|---|---|---|
| 4,907,158 | 3/1990 | Kettler et al. | 364/413.01 |
| 5,229,679 | 7/1993 | Higuchi et al. | 310/328 |
| 5,325,289 | 6/1994 | Togawa | 364/167.01 |
| 5,332,071 | 7/1994 | Conway et al. | 294/100 |
| 5,451,924 | 9/1995 | Massimino et al. | 340/407.1 |
| 5,784,542 | 7/1998 | Ohm et al. | 395/95 |
| 5,865,426 | 2/1999 | Kazerooni | 254/270 |

OTHER PUBLICATIONS

Kazerooni, "The Extender Technology at the University of California, Berkeley," J. SICE vol. 34, No. 4, pp. 291–298 (Apr., 1995).

Kazerooni and Guo, "Human Extenders," ASME J. Dynamic Systems, Measurements and Control, 115–2(B) (Jun., 1993).

Kazerooni and Her, "A Virtual Exercise Machine," IEEE, pp. 232–238 (1993).

Kazerooni, "Issues on the Control of Robotic Systems Worn by Humans," pp. 386–388 (1992).

Kazerooni and Mahoney, "Dynamics and Control of Robotic Systems Worn By Humans," ASME J. Dynamic Systems, Measurements and Control, pp. 379–387 (Sep., 1991).

Kazerooni, "Human–Robot Interaction via the Transfer of Power and Information Signals," IEEE Transactions on Systems and Cybernetics, 20–2 (Mar., 1990).

Kazerooni and Foslien, "On the Control and Stability of Robots Worn by Human: Theory," American Control Conference, pp. 1918–1924 (Jun., 1989), Pittsburgh, Pennsylvania.

Kazerooni and Hessburg, "On the Control and Stability of Robots Worn by Human: Experiments," American Control Conference, pp. 1925–1930 (Jun., 1989), Pittsburgh, Pennsylvania.

Kazerooni, "Human/Robot Interaction via the Transfer of Power and Information Signals Part I: Dynamics and Control Analysis," IEEE, pp. 1632–1640 (1989).

Kazerooni, "Human/Robot Interaction via the Transfer of Power and Information Signals Part II: An Experimental Analysis," IEEE, pp. 1641–1647 (1989).

GE Company, "Final Report on Hardiman I Prototype for Machine Augmentation of Human Strength and Endurance," Schenectady, New York (1971).

GE Company, "Hardiman I Prototype Project: Special Interim Study," Report s–68–1060, Schenectady, New York (1968).

*Primary Examiner*—Bentsu Ro
*Attorney, Agent, or Firm*—Lockheed Martin Energy Research Corporation

[57] ABSTRACT

A human de-amplifier system for interfacing a human operator and a physical object through a physical plant, wherein the physical object has dimensions in the range of 1 micrometer to 1 mm. The human de-amplifier system uses an inner-feedback loop to increases the equivalent damping of the operating system to stabilize the system when it contacts with the environment and reduces the impact of the environment variation by utilizing a high feedback gain, determined by a root locus sketch. Because the stability of the human de-amplifier system of the present invention is greatly enhanced over that of the prior art, the de-amplifier system is able to manipulate the physical object has dimensions in the range of 1 micrometer to 1 mm with high stability and accuracy. The system also has a monitoring device to monitor the motion of the physical object under manipulation.

32 Claims, 6 Drawing Sheets

APPARATUS AND METHODS FOR A HUMAN DE-AMPLIFIER SYSTEM

This invention was made with Government support under Contract No. DE-AC05-84OR21400 awarded by the U.S. Department of Energy to Lockheed Martin Energy Research Corp., and the Government has certain rights in this invention.

BACKGROUND OF THE INVENTION

1. Field of the Invention

The present invention comprises an apparatus and methods for a human de-amplifier system. In particular, the invention relates to an apparatus and methods for a human de-amplifier system capable of interfacing a human operator and a physical object with miniature dimensions so that the physical object can be dexterously manipulated.

2. Background Art

Teleoperated manipulator has long been developed to perform tasks which would otherwise be performed by humans. Conventionally, a teleoperated manipulator has a separate master-slave system. The human operator, as the master, may be either at a remote location or close to the slave manipulator, but the human is not in direct physical contact with the slave manipulator. The human master can exchange information signals with the slave, but not mechanical power. Therefore, the input signal to the slave is derived from a difference in the control variables (i.e., position, velocity, or other kinetic parameters) between the human master and the slave manipulator, but not from any set of contact forces.

While conventional teleoperated manipulator with the master-slave design is successful in performing many tasks, there are numerous human activities that require human operators performing tasks that demand their intelligence and physical strength often beyond their capability. These tasks cannot be best performed by a traditional robot manipulator because these tasks need a spontaneous information signal and power transfer between the human operator and the working environment, which cannot be provided by the traditional robot manipulator with a master-slave design. Consequently, human extender, a new species of robot manipulator has been developed over the years.

A human extender is a device that amplifies the lifting capacity of a human operator and allows a preselected amount of force feedback to the operator (i.e., the operator can feel part of the load). This type of system is fundamentally different from a teleoperator system because the master and slave manipulators are a single unit in a human extender. This concept was first developed in the 1960's by General Electric during the Hardiman project, as documented in the publications of "Special Interim Study, Hardiman I Prototype Project," Report S-68-1060, General Electric Company, Schenectady, N.Y., Apr. 19, 1968, "Hardiman I Arm Test, Hardiman I Prototype Project," Report S-70-1019, General Electric Company, Schenectady, N.Y., Dec. 31, 1969, and "Final Report on Hardiman I Prototype for Machine Augmentation of Human Strength and Endurance," General Electric Company, Schenectady, N.Y., Aug. 30, 1971. More recently, Kazerooni disclosed a scaled down version of a similar concept in the papers of "Human/Robot Interaction via the Transfer of Power and Information, Part I: Dynamics and Control Analysis," Kazerooni, H., EKE Robotic and Automation Conference, pp. 1632–1640 (Scottsdale, Ariz., 1989), "Human/Robot Interaction via the Transfer of Power and Information, Part 2: An Experimental Analysis," Kazerooni, H., EKE Robotic and Automation Conference, pp. 1641–1647 (Scottsdale, Ariz., 1989), "Human-Robot Interaction via the Transfer of Power and Information Signal," Kazerooni, H., EKE Transaction on Systems, Man, and Cybernetics, Vol. 20, No. 2, pp. 450–463 (1990), and "Human Extenders," Kazerooni, H., J. Guo, Journal of Dynamic Systems, Measurement, and Control, Vol. 115, pp. 281–290 (1990).

The human extender concept is developed in order to take benefit from the strength advantage of robot manipulators and the intellectual advantage of human beings. An important feature of the human extender system is that the input signal to the extender is derived from the set of contact forces between the extender and the human operator. In other words, force reflection occurs naturally in a human extender. Because there is no separate set of actuators, the human hand feels the actual forces on the extender, both direction of motion and a scaled-down version of the load. For example, if a human extender manipulates a 500 lbs. object, the human operator may just feel 10 lbs. while the extender supports the rest of the load. This 10 lbs. contact forces are used not only for manipulation of the object, but also for generating the appropriate signals to the extender controller. The capability of a human extender is often measured by its force reflection ratio, which is defined as the ratio of the real load to the forces the human feels. For the example just given, the force reflection ratio is 50 to 1.

Many potential uses are available for human extender. For example, in an unstructured environment, military personnel often need to use special equipment such as weapon loader to manipulate and orient large objects. An equipment capable of transmitting back to the operator a fraction of the object's dynamics (e.g., its weight, contact forces, slippage, etc.) could significantly enhance productivity, quality, and safety. A human extender can be integrated into a weapon loader to perform such tasks.

Similarly, a human extender can find a wide area of civic use in fields such as the package-delivery service industry. Package-delivery companies, such as United Parcel Service of America, Inc. (UPS), have increased their weight limit on the boxes they carry gradually. UPS has gone from 70 pounds to 150 pounds in order to remain competitive. UPS has also experience a 2 to 3% higher lost time due to injuries than similar types of businesses. A typical job at a UPS hub requires lifting and sorting up to 900 boxes an hour and placing them on a dozen conveyor belts. A dextrous device that has a large work space and can handle large payloads, while utilizing the intelligence of the operator to spontaneously generate the command signal to handle the loads repeatedly, safely, accurately and efficiently, could have a significant impact in the package-delivery service industry. Similar devices can find their use in manufacture assembly lines, in rescue operations, in construction industry and many other areas.

However, a number of problems associated with the available human amplifier systems. Profound instabilities due to gross nonlinearities in the fluid power system (e.g., nonlinear pressure-flow relationship, time varying fluid properties, large quantities of nonlinear friction, time varying system dynamics) and differences in human operator dynamics rendered the system impractical for large force gains as discussed in the paper of "Human-Robot Interaction via the Transfer of Power and Information Signal," Kazerooni, H., EKE Transaction on Systems, Man, and Cybernetics, Vol. 20, No. 2, pp. 450–463 (1990). These instabilities occur when the human extender makes contact with the environment. To overcome these instabilities, a computed torque technique was used with a proportional plus derivative law ("PD") controller as the primary stabilizing controller as disclosed in the paper of "Human Extenders," Kazerooni, H., J. Guo, Journal of Dynamic Systems, Measurement, and Control, Vol. 115, pp. 281–290 (1990). Unfortunately, computed torque technique is a model based scheme that requires significant knowledge about the physical system plus it represents a significant computational burden on the controller. Computed torque can be rendered basically useless if the model is just a few percent off of the calculated value.

A one-axis human amplifier system is described in U.S. Pat. No. 5,865,426 issued to Kazerooni. Upward vertical forces such as gravity and inertia are reduced to the human operator through this system when picking up a load such as a heavy box. The load is attached to a single actuator through a wire rope. Since wire rope can react only to tension type loads this system is suitable for lifting objects only in the upward vertical direction. This system is deficient for tasks that require forces in both the upward and downward directions or if forces and moments are required in other planes of motion.

Moreover, the currently available human extenders are specifically designed for extending the human operator's physical strength to lift more or manipulate large objects. However, in the real world, there are many occasions that manipulating small objects poses challenge to human beings. For example, in performing surgeries including laparoscopic techniques, doctors need to move small physical objects around. In micro assembly of electrical components, such as chip-making manufacture lines, tasks need to be performed on objects with micro dimensions. In modern biotech labs, biological specimens in micro, even nano dimensions need to be manipulated. These activities require human operators to perform tasks that demands their intelligence and well controlled physical strength. However, just as humans cannot move the objects at will beyond their physical strength without help, they often have difficult time to locate, move, or manipulate the objects that can be easily disturbed by a fraction of their physical strength.

Therefore, there is a need to develop a device capable of dexterously manipulating small objects with the dimension in the range of 1 micrometer to 1 mm. Conventional electronically coupled teleoperated systems are incapable of performing such tasks because they have inherent system stiffness. Neither can currently available human extenders deliver satisfactory performance because they have profound instabilities.

SUMMARY OF THE INVENTION

Definitions

A number of abbreviations used in this application for some frequently used technical terms are defined as the following:

The term "$D_{act}$" as used herein shall refer to drive signal to servo drive cards.

The term "$F_{act}$" as used herein shall refer to actuator forces or moments vector.

The term "$F_{hand}$" as used herein shall refer to hand forces and moments vector.

The term "$F_{env}$" as used herein shall refer to environment reaction forces and moments vector.

The term "$\theta_{jnt}$" as used herein shall refer to angular position vector of joint angles or joint displacements.

$F_{act}$, $F_{hand}$ and $F_{env}$ are typically 6×1 vectors. The term "force(s)" as used herein shall refer to force(s) or moment(s) or combination of force(s) and moment(s).

Summary

The present invention overcomes the disadvantages of the prior art and discloses a human de-amplifier system. The human de-amplifier includes a human de-amplifier controller, a monitoring device, and a human de-amplifier physical plant. The human de-amplifier controller interfaces between a human operator and the human de-amplifier physical plant through a handle with force sensors mounted therein. The physical plant is driven by at least one actuator. The human operator applies forces to the handle in a normal way as to move a physical object in normal world. These sensors generate contact force signals and transfer them to the controller. Moreover, force sensors can also be installed to measure the interaction between the physical plant and the physical object to generate interacting force signals. Similarly, force sensors can also utilized to measure the force caused at the actuator by the interaction between the physical plant and the physical object to generate actuating force signals. The controller processes these force signals and scales the signals to produce drive signals. The actuator then receives these drive signals and in turn drive the physical plant so that the force exerted on the physical object is controlled to the desired value scaled from the input handle. The monitoring device provides spontaneous motion signals of the physical objects and displays the signals in a visual display so that the human operator can constantly check the positions of the physical object and adjust the force accordingly. The controller utilizes at least one inner-feedback loop to increase the equivalent damping of the operating system to stabilize the system when it contacts with the environment and a compensator with a high gain feedback to reduce the impact of the environment variation. As disclosed in the patent application filed concurrently, "Apparatus and Methods for a Human Extender," which is fully incorporated here as part of this application by reference, the stability of the human de-amplifier controller of the present invention is greatly enhanced over that of the prior art. Thus, the controller of the present invention is able to manipulate the physical objects with the micro and nano dimensions.

According to one preferred embodiment of the present invention, a system for interfacing a human operator and a physical object through a physical plant, wherein the physical plant is driven by at least one actuator and has dimensions in the range of 1 micrometer to 1 mm, has means for providing drive signals, means for using the drive signals to manipulate the physical object, and means for monitoring the motion of the physical object. The means for providing drive signals includes means for generating incoming signals, wherein the incoming signals include contact force signals representative of forces from the hand of the human operator interacting with the surrounding environment, interacting force signals representative of forces caused at the physical plant by the interaction between the physical plant and the physical object, and actuating force signals representative of forces caused at the actuator by the interaction between the physical plant and the physical object, means for compensating at least partially the incoming signals directly in response to variations of the environment, and means for generating drive signals from the at least partially compensated signals.

The system for interfacing a human operator and a physical object through a physical plant, wherein the physical plant is driven by at least one actuator and has dimensions in the range of 1 micrometer to 1 mm, in another preferred embodiment, has a controller and a monitoring device. The controller includes at least one first force sensitive device for generating contact force signals representative of forces from the hand of the human operator interacting with the surrounding environment, at least one second force sensitive device for generating interacting force signals representative of forces caused at the physical plant by the interaction between the physical plant and the physical object, and at least one third force sensitive device for generating actuating force signals representative of forces caused at the actuator by the interaction between the physical plant and the physical object. The controller also has a compensator for compensating the contact and interacting force signals, wherein the compensator is capable of producing high feedback gain. The controller further has an inner-feedback loop having a constant gain for compensating the actuating force signals, where the inner-feedback loop includes a load cell. The controller additionally has a limiter receiving the compensated contact force signals, interacting force signals and actuating force signals, and thereby generating drive signals for manipulating the physical object, so that the actuator receives the drive signals and uses the drive signals to manipulate the physical object through the physical plant. The monitoring device is connected to the controller, providing the controller information related to the positions of the physical object. The monitoring device includes a visual display to interface with the human operator.

According to still another embodiment, the present invention provides a method for interfacing a human operator and a physical object through a physical plant, wherein the physical object has dimensions in the range of 1 micrometer to 1 mm and the physical plant is driven by at least one actuator, by providing drive signals, using the drive signals to manipulate the physical object, and monitoring the motion of the physical object. The providing step includes generating contact force signals representative of forces from the hand of the human operator interacting with the surrounding environment, generating interacting force signals representative of forces caused at the physical plant by the interaction between the physical plant and the physical object, generating actuating force signals representative of forces caused at the actuator by the interaction between the physical plant and the physical object, receiving and filtering the contact force signals and interacting force signals, compensating the actuating force signals, generating drive signals from the contact force signals, interacting force signals and actuating force signals, and using the drive signals to manipulate the physical object through the physical plant.

Practicing the present invention according to this method also includes the steps of changing the contact force signals and interacting force signals into equivalent Cartesian velocity signals, converting the Cartesian velocity signals into joint velocity signals by inverting a manipulator-specific Jacobian matrix, and compensating the joint velocity signals with high gain feedback. Additionally, practicing the present invention needs solving a characteristic equation of transfer function to determine the gain to reduce overshooting to a step response.

Other advantages and uses for the present invention will be more clearly understood by reference to the remainder of this document.

DETAILED DESCRIPTION OF THE INVENTION

The present invention is more particularly described in the following examples that are intended as illustrative only since numerous modifications and variations therein will be apparent to those skilled in the art. As used in the specification and in the claims, "a" can mean one or more, depending upon the context in which it is used. The preferred embodiment is now described with reference to the FIGS. 1–7, in which like numbers indicate like parts throughout the FIGS. 1–7.

Referring generally to FIGS. 1–7, the present invention comprises a human de-amplifier system that offers a stable and less computational intensive interface between a human operator and a human de-amplifier physical plant. The present invention provides a substantially stable human de-amplifier capable of handling physical objects with dimensions in the range of 1 micrometer to 1 mm.

Figure 1:
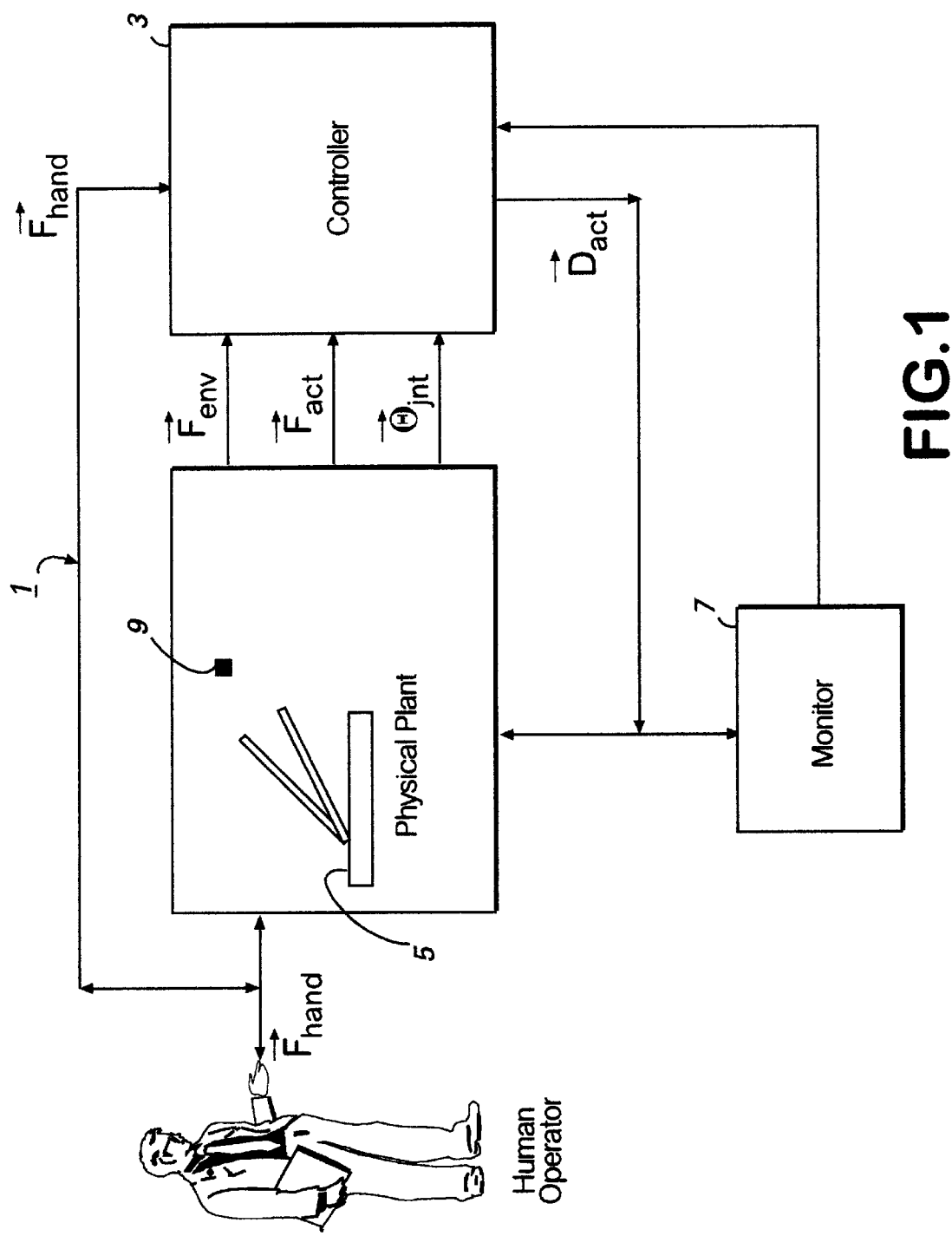
FIG. 1 is a high level functional diagram showing the exchange of information between the controller, the physical plant, the monitoring device and the human operator.
Figure 2:
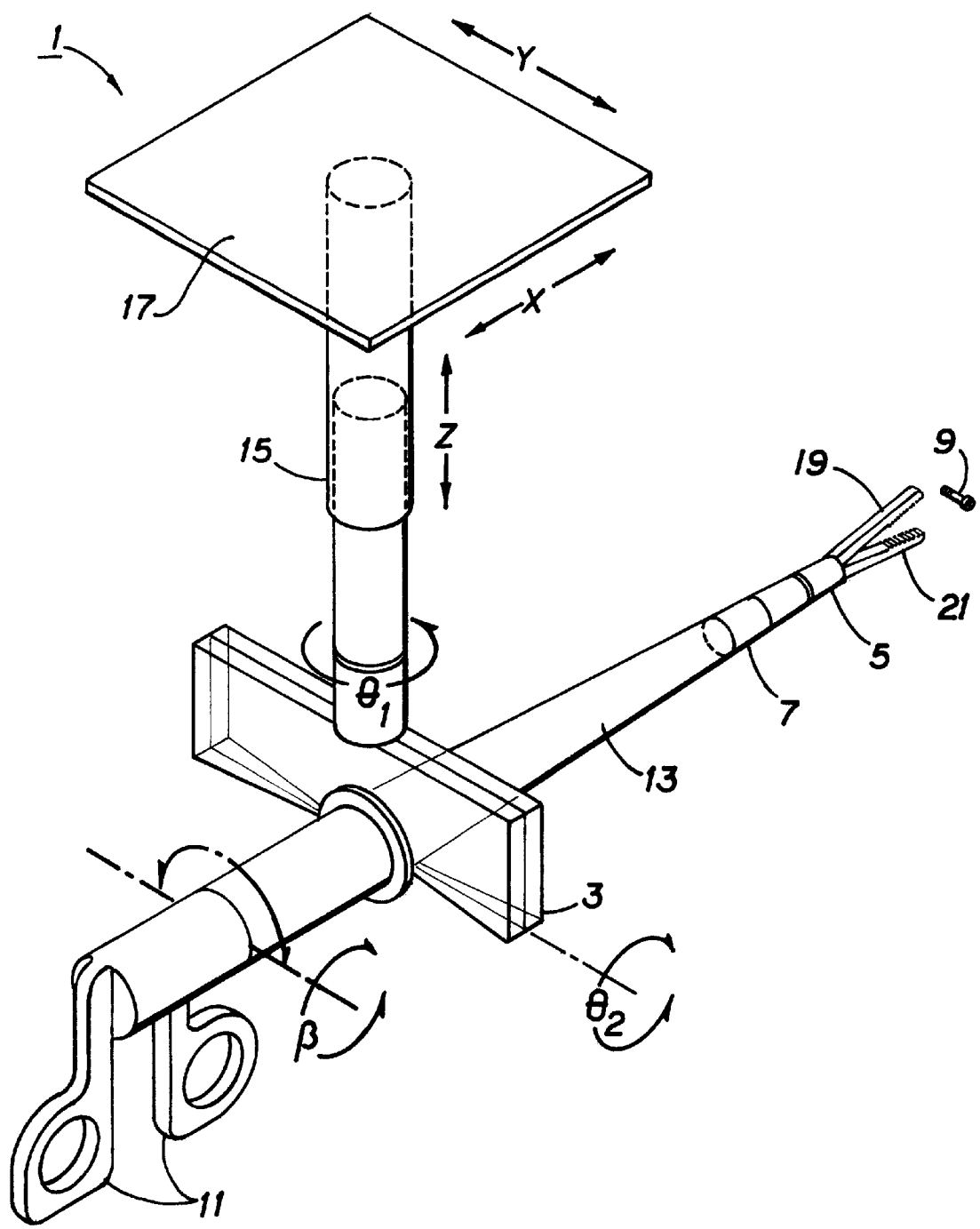
FIG. 2 schematically shows a laparoscopic surgery handler according to one embodiment of the present invention.

Referring to FIG. 1, human de-amplifier system 1 of the present invention has a controller 3, a physical plant 5 and a monitoring device 7. The controller 3 interfaces between a human operator and the physical plant 5, which in turn manipulates physical object 9. During the manipulation, the hand of the human operator interacts with the surrounding environment, say handle 11 as shown in FIG. 2, thus exerts force on the handle. This force is measured by a force sensitive device to produce contact force signals, $F_{hand}$. Similarly, the interaction between the physical plant 5 and the physical object 9 generates interacting force signals, $F_{env}$. Moreover, because the physical plant 5 is driven by at least one actuator, the interaction between the physical plant 5 and the physical object 9 during the manipulation causes a force exerting on the actuator, which can also be measured to generate actuating force signals, $F_{act}$. In use, the controller 3 receives the incoming force signals, $F_{hand}$, $F_{env}$ and $F_{act}$, and produces corresponding drive signals, $D_{act}$, to manipulate the physical object 9 through the physical plant 5.

The monitoring device 7 monitors the motions of the physical object 9 and the physical plant 5 and communicates the information to the human operator through controller 3. The capability of a human de-amplifier controller is measured by its force amplifying ratio. Assuming that the physical object 9 weighs 1 g ("$F_{env}$") and human de-amplifier controller 3 has a force amplifying ratio 500, the human operator would "feel" 500 g forces ("$F_{hand}$"). The 499 g "extra" forces (500 g–1 g) are absorbed by the system during the contact between the human operator and the system. The 500 g contact forces are used not only for manipulation of the object 9, but also for generating the appropriate drive signals ("$D_{act}$") through controller 3 to physical plant 5 to supply proper forces to perform the task the human operator is doing, namely, manipulating the object 9. Human de-amplifier physical plant 5, in one embodiment of the present invention, is driven by hydraulic actuators to provide forces. Other mechanisms, such as electrical actuators, electrical-hydraulic actuators, mechanical actuators, or any combination of them, can also be easily adopted to generate forces needed to perform various tasks.

Monitoring device 7 is used to detect and monitor the motions of the object 9 and the physical plant 5. Because the object 9 has dimensions in the range of 1 micrometer to 1 mm, naked eyes can hardly detect its motion. Monitoring device 7 thus provides a channel for the human operator to follow the motion of the object 9 under manipulation and therefore to manipulate the object properly. Monitoring device 7 may be an optical instrument containing one or a number of optical lens to transfer and amplify the image of the object 9. Alternatively, monitoring device may be an electronic device having data collector, data transmitter and data display (not shown). The data collector can be motion detectors capable of gathering information about the motion of the object 9. The data transmitter can be a cable, or a wireless device. The display can be a TV, a monitor or a computer with a computer screen. It is preferred to use a computer as part of the monitoring device because the data can be saved and then displayed repeatedly. Moreover, the data can be shared over a computer network.

Referring now to FIG. 2, where a laparoscopic surgery handler according to one embodiment of the present invention is schematically shown. Handler 1 can be used to manipulate a small object 9. Handler 1 has an elongated, hollow body 13. Attached at one end of the body 13 is a tool head 5 with two arms 19, 21 associated with. Arms 19, 21 are positioned so that when they need to catch and hold the object 9, they move toward to each other. Conversely, they move away from each other to release the object 9. Obviously, more than two arms can be installed on the tool head 5. A monitoring device 7 is connected to the tool head 5. At the other end of the elongated body 13 are two handles 11 with force sensitive devices installed therein. The controller 3 is located at the middle of the body 13. The body 13 is pivotally supported by a tube 15, which in turn is connected to a supporting plane 17. Additionally, the elongated body 13 can rotate about its longitudinal axis. In total, the space position and orientation of the handler 1 can be adjusted through adjusting Cartesian parameters, x, y, and z, and angular parameters, $\theta_1$, $\theta_2$, and $\beta$ as shown in FIG. 2.

Figure 3:
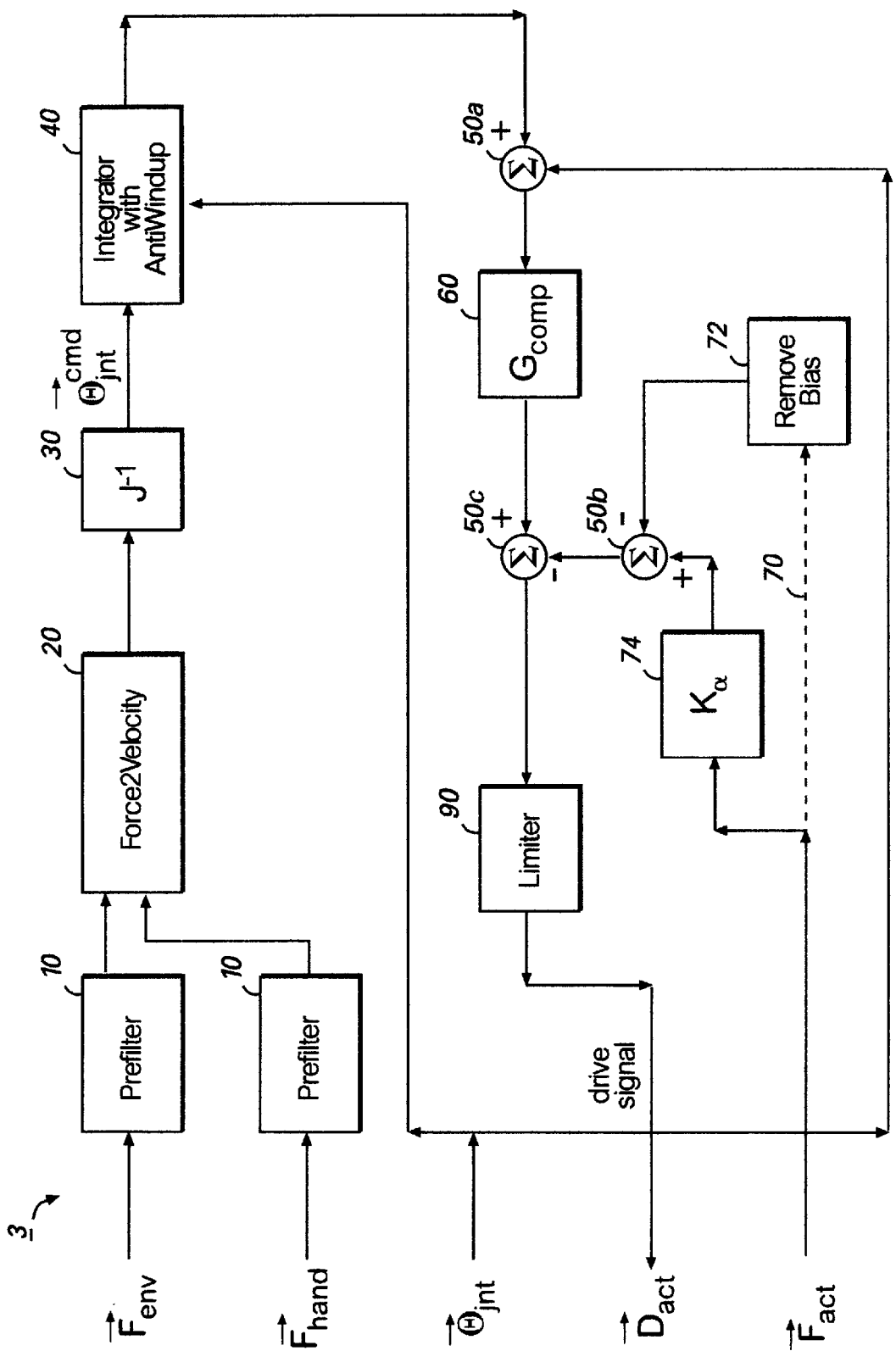
FIG. 3 displays a block diagram for a velocity based human de-amplifier controller according to a preferred embodiment of the present invention.

In order for the de-amplifier 1 to manipulate small objects, controller 3 must be able to operate stably. The controller 3 according to the present invention uses a high gain feedback compensator and an inner feedback loop to achieve the stability. FIG. 3 shows a first embodiment of the human de-amplifier controller 3 according to the present invention. In FIG. 3, human de-amplifier controller 3 is a velocity-based human de-amplifier controller. Human de-amplifier controller 3 includes at least one prefilter or filter 10 to receive the force signals from the human operator and the environment and to eliminate noise from the force signals. Among many available choices of filters available, the present invention uses either a first or a second order lag filter. A combination of a first and a second lag filter can also be utilized. The force signals can be collected by force sensitive devices such as force/torque sensors or load cells. A preferred type of force sensitive devices is a strain gauge type transducer. Alternatively, a semi-conductor based gauge type transducer can also be used. The force signals collected at a force sensitive device include three components of force and three components of torque present at any three-dimensional coupling between two objects. These sensors can be mounted on a handle, such as handles 11 as shown in FIG. 2, on a glove, or on other structures to provide direct contact between a human operator and the human de-amplifier.

Referring to FIG. 3, as shown in block 20, the filtered contact and interacting force signals from prefilter(s) 10 are then changed into an equivalent velocity signal according to the following rule:

$$v = A_{joy} F_{hand} - A_{ext} F_{env}$$

where $A_{joy}$ is a joystick accommodation matrix (typically 6×6), $A_{ext}$ is an external accommodation matrix (typically 6×6), and v is the Cartesian velocity vector (typically 6×1). Optionally, logical statements can be programmed into block 20 to establish a threshold force to ensure that the human de-amplifier controller 3 is activated only when $F_{env}$ passes the threshold. An index switch (not shown) may be utilized to trigger the operation of the logical statements. Although v now appears as a velocity vector, however, it contains the information embodied in the force signals $F_{env}$ and $F_{hand}$. Moreover, $A_{joy}$ and $A_{ext}$ can be programmed to achieve the desired force reflection ratio.

The Cartesian velocity v is converted into joint velocity at a conversion block 30. This conversion is typically performed by inverting a matrix called the manipulator Jacobian ("J"). The matrix elements of J are manipulator specific, as known by people skilled in the art. The inversion process involves inverting a square matrix that is nonsingular. However, if the manipulator has more degrees-of-freedom then required to perform a task (i.e., it is mechanically redundant) then the inversion process optimizes some performance criteria.

The joint velocity signals are then integrated at integration block 40. Integration block 40 at least has an integrator with antiwindup capability or limits on upper bounds of the integrated signals. In other words, block 40 integrates the incoming joint velocity signals with the restriction that if a joint limit is reached it will limit the output to the joint limit value without allowing the integrator term to build up.

The integrated joint velocity signals, combined with the signals containing information about joint displacements ("$\theta_{jnt}$"), are summed at block 50. Then, still referring to FIG. 3, compensation block 60 utilizes a compensator with a high gain feedback, $G_{comp}$, to compensate the incoming signals from block 50. Preferably, $G_{comp}$ is a proportional type or lag-lead type compensator. For a sufficient high amplification gain value, say $K_{comp}$, the affect of plant variation due to load, fluid temperature variation, fluid bulk modulus and other disturbances can be reduced and thus the likelihood of system instability is reduced. The value of $K_{comp}$ can be chosen as a constant or a value determined by solving a characteristic equation using the root locus sketch as known by people skilled in the filed and further discussed in a simplified single degree-of-freedom system vide infra.

Similarly, the incoming actuating force signals, $F_{act}$, are also sensitive to the variation of the environment including variation of the physical object 9. An inner-feedback loop 70 is utilized here to increase the equivalent damping of the operating system to stabilize it when the physical plant 5 contacts with the environment. Without this inner-feedback loop, the position of the physical plant 5 may oscillate when contact with the environment is made. The inner-feedback loop 70 contains a zeroing block 72, a vector gain block 74 and a summation block 50b. Block 72 removes bias from the incoming actuating signals by, for example, zeroing the signals at startup. Block 74 feeds the actuating force signals once the bias values are removed therein. The block 74 is characterized by an actuator force or moment gain, Kα, which is chosen as a constant in this embodiment of the present invention. The inner-feedback loop 70 may also include a load cell, a clevis pin, an accelerometer, or other instrument for measurement of the incoming actuating force signals. Because the high gain feedback block 60 and the inner-feedback loop 70 respond directly to the variations of the environment, the controller 3 has a high tolerance for these variations and thus achieves stability over a wide range of variations of the environment. Moreover, because the utilization of high gain feedback block 60 and inner-feedback loop 70, the use of model-based approach such as computed-torque method is eliminated. The present invention hence requires less computing capacity without compromising the stability of the controller.

All incoming signals, now properly processed, are summed at summation block 50c and introduced into a limiter 90. Limiter 90 limits the upper and lower bounds of the incoming signals so that outgoing signals are confined within a range. These outgoing signals are driving signals, $D_{act}$, which are distributed by the limiter 90 to proper servo driver card(s) (not shown) connected to the actuator(s) (not shown). The actuator(s) then drive the physical plant 5 to manipulate the physical object 9 accordingly.

Figure 4:
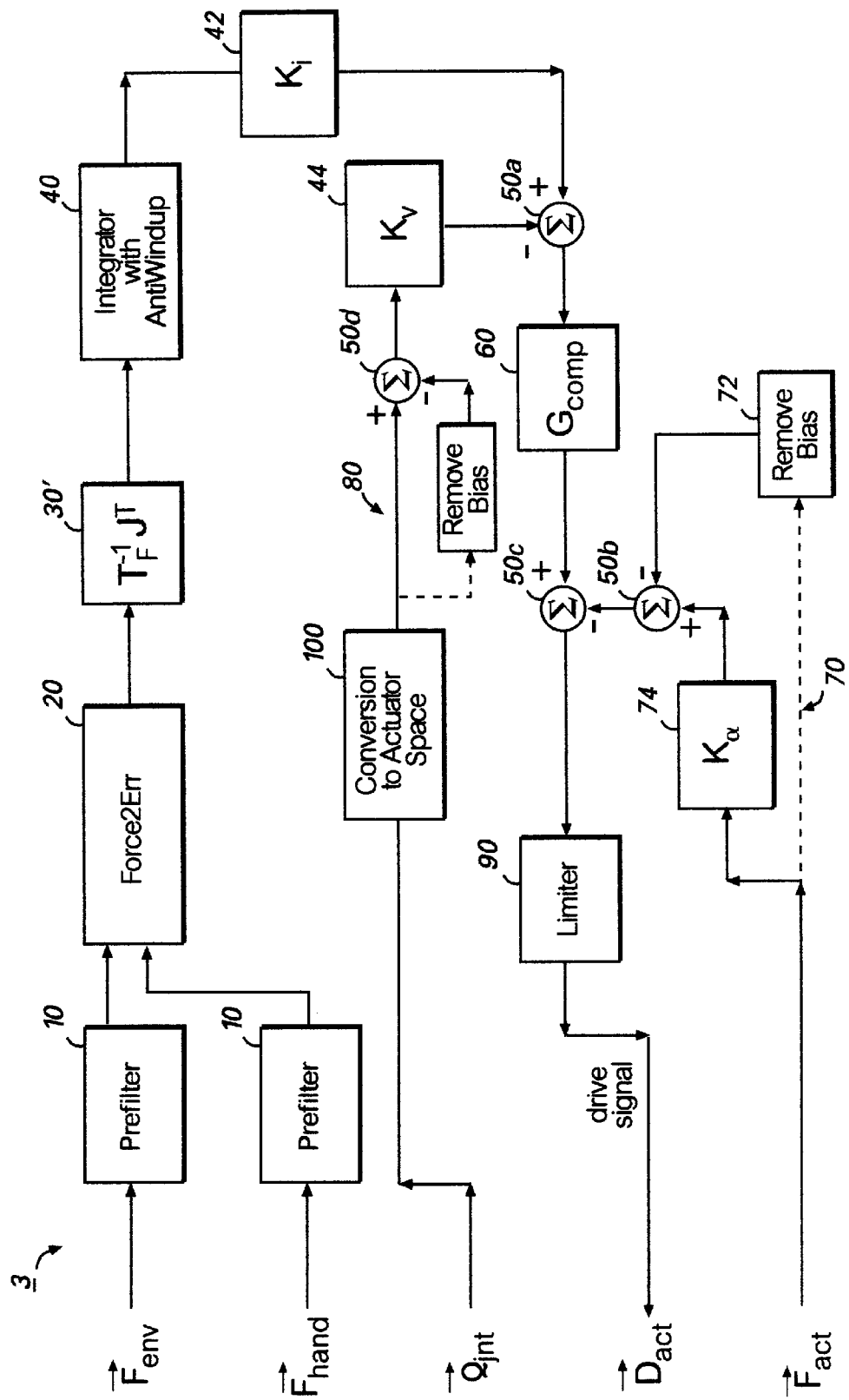
FIG. 4 displays a block diagram for an acceleration based human de-amplifier controller according to another preferred embodiment of the present invention.

FIG. 4 shows another embodiment of the human de-amplifier controller 3 according to the present invention. In FIG. 4, human de-amplifier controller 3 is an acceleration-based human de-amplifier controller. Instead of converting the force signals into an equivalent velocity signal in the embodiment shown in FIG. 3, Force2Error block 20 receives the filtered contact and interacting force signals from prefilter(s) 10 and changes the force signals into an equivalent acceleration signal according to the following rule:

$$f = B_{joy} F_{hand} - B_{ext} F_{env}$$

where $B_{joy}$ is a joystick accommodation matrix (typically 6×6), $B_{ext}$ is an external accommodation matrix (typically 6×6), and f is the Cartesian force vector (typically 6×1). Again, logical statements may be programmed into block 20 to establish a threshold force to ensure that the human de-amplifier controller 3 is activated only when $F_{env}$ passes that threshold.

The Cartesian force f is subsequently converted into actuator forces at conversion block 30'. This conversion is typically performed by multiplying the transpose of the manipulator Jacobian ("J") with the inverse of the transmission ratio matrix ("$T_F$") that relates the joint moments to the actuator forces or actuator moments.

The converted signals are integrated at integration block 40 that has an integrator with antiwindup capability. After passing the integrator vector gain block 42, which is characterized by a force feedback gain $K_i$, the integrated force signals summed with $\theta_{jnt}$ at summation block 50a. The joint displacement signals $\theta_{jnt}$ has been converted into actuator space at conversion block 100 and the bias in $\theta_{jnt}$ has been removed through inner loop 80, which includes a summation block 50d.

Again, the incoming signals are compensated at compensation block 60 by a compensator $G_{comp}$ with a high amplification gain $K_{comp}$, where $K_{comp}$ can be chosen as a constant or a value determined by solving a characteristic equation using the root locus sketch, as well as by an inner-feedback loop 70 to increase the equivalent damping of the operating system. As discussed above, the high gain compensator 60 and the inner-feedback loop 70 respond directly to the variations of the environment and therefore are able to stabilize the system over a wide range of variations of the environment.

Figure 5:
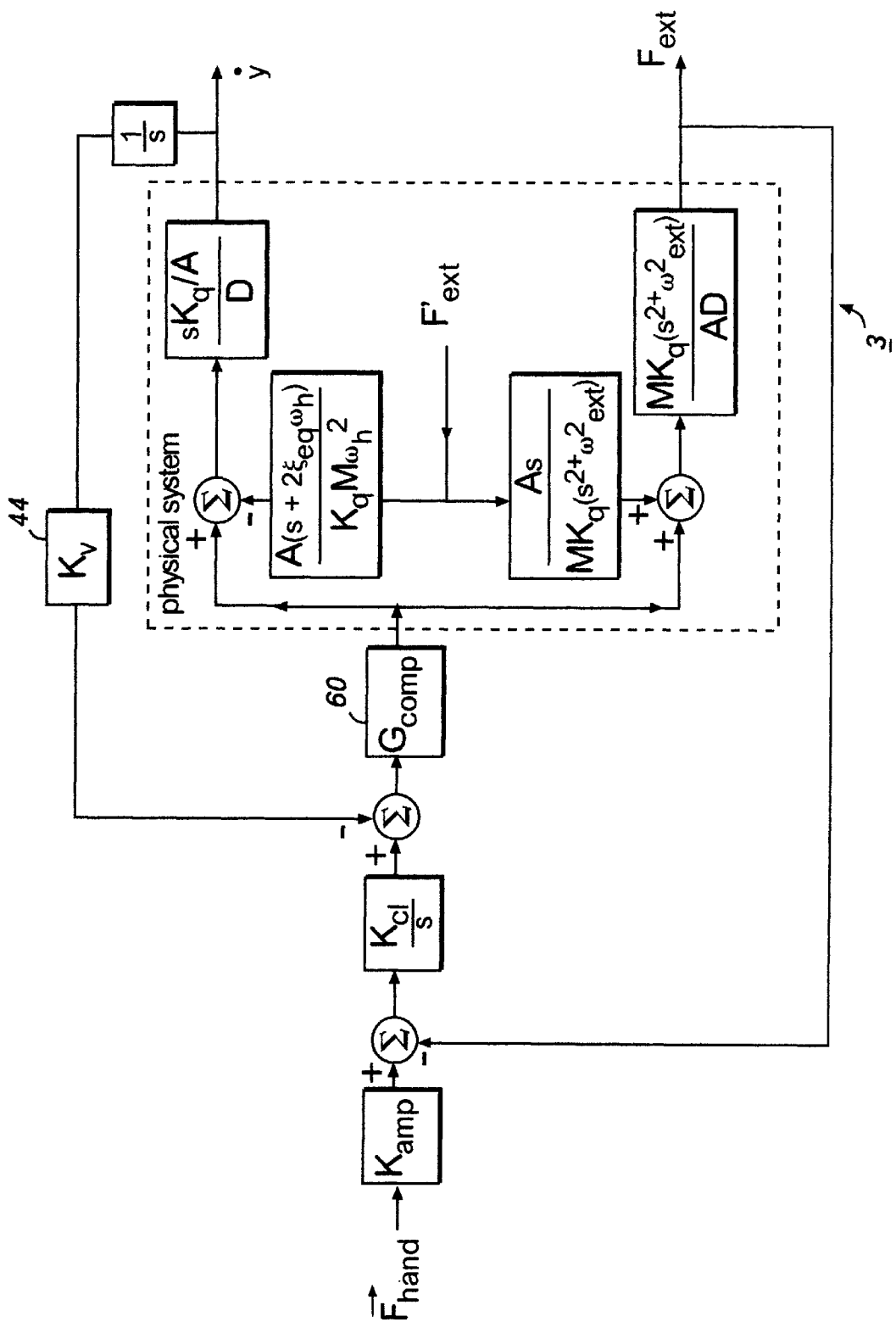
FIG. 5 displays a block diagram for a human de-amplifier controller according to a preferred embodiment of the present invention for a linearized one degree-of-freedom system.
Figure 6:
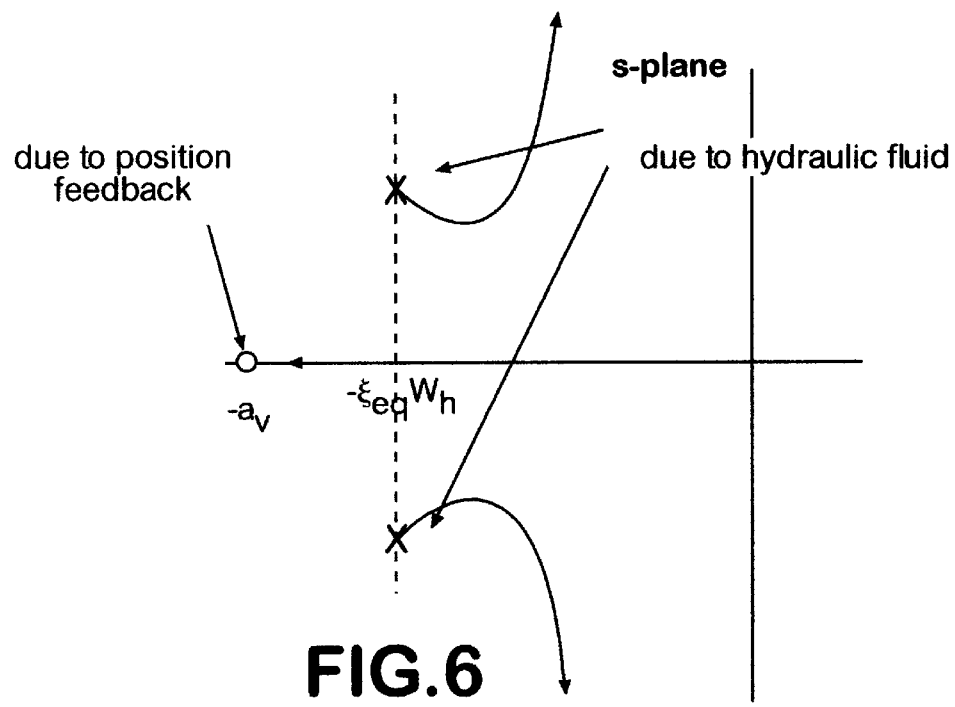
FIG. 6 schematically shows Root Locus of the characteristic equation for the system shown in FIG. 5.

The invention, especially the process to choose the value of gain $K_{comp}$ by solving a characteristic equation using the root locus sketch, will be better understood by reference to the following single degree-of-freedom embodiment, which is illustrated in FIG. 5.

A Single Degree-of-Freedom Embodiment

The physical plant is driven by actuators through mechanical joints. The movement of the joints causes the physical plant to interact with the physical object. Typically, dynamic interactions between joints are relatively insignificant since each actuator drives each joint directly. Furthermore, slow to moderate manipulator speeds are typical for routine manipulation. For these reasons, a single degree-of-freedom system is sufficiently accurate to represent the salient dynamics of the manipulator systems. FIG. 5 illustrates a block diagram of such a single degree-of-freedom system, where the electro-hydraulic system has been linearized with the assumption that hand forces interaction with the payload are insignificant.

Definition of Symbols for FIG. 5

A=effective cylinder area of a hydraulic container
$D = s(s^2/\omega_h^2 + 2s\xi_{eq}/\omega_h + 1) + (\omega_{ext}/\omega_h)^2(s + 2\xi_{eq}\omega_h)$
$F_{ext}$=external force measured by sensor
$F'_{ext}$=external force due to contact
$F_{hand}$=hand force
$G_{comp}$=proportional or lag-lead type compensator
$K_{amp}$=amplification gain of the human de-amplifier
$K_\alpha$=actuator force or moment feedback gain
$K_{cli}$=integrator gain
$K_q$=flow gain
$K_v$=position feedback gain (behaves like velocity damping)
M=mass of load
s=Laplace operator
y=actuator velocity
ẏ=actuator position
$\alpha_v = K_v / K_{cli}$
$\xi_h$=hydraulic damping ratio
$\xi_{eq}$=equivalent damping=$\xi_h + (MK_q K_\alpha \omega_h)/(2A)$
$\omega_h$=hydraulic natural frequency
$\omega_{ext}$=external natural frequency (assuming spring type load, will be zero if load is not a spring as the case discussed vide infra)

Discussion of the Embodiment Shown in FIG. 5

Two transfer functions can be obtained from FIG. 5. The first is the transfer function from the force at the hand, $F_{hand}$, to the actuator velocity, ẏ, with the external force due to the contact, $F'_{ext}$, set to zero $$\dot{y}T_{Fhand} = [K_{amp}K_{cli}G_{comp}(K_q/A)]/[s(s^2/\omega_h^2 + 2s\xi_{eq}/\omega_h + 1) + M K_{cli}G_{comp}(K_q/A)(s + a_v)] \quad (1)$$

with the assumptions that the load will be a constant load and not a spring type load (i.e., $\omega_{ext} = 0$). The second transfer function is the one that relates the external force due to contact, $F'_{ext}$, to actuator velocity, ẏ, with the force at the hand, $F_{hand}$, set to zero $$\dot{y}T_{Fext} = (-1/M)[s^2/\omega_h^2 + 2s\xi_{eq}/\omega_h + M K_{cli}G_{comp}(K_q/A)]/[s(s^2/\omega_h^2 + 2s\xi_{eq}/\omega_h + 1) + M K_{cli}G_{comp}(K_q/A)(s + a_v)] \quad (2)$$

with the assumption that the load will be a constant load and not a spring type load (i.e., $\omega_{ext} = 0$).

If the compensator 60, $G_{comp}$, is set to a proportional gain denoted by $K_{comp}$, then the characteristic equation for both transfer functions is the same as follows $$s(s^2/\omega_h^2 + 2s\xi_{eq}/\omega_h + 1) + M K_{cl} K_{comp}(K_q/A)(s+a_v) = 0 \qquad (3)$$

which represents the equivalent root locus problem with $K_{comp}$ as the variable. The root locus of the characteristic equation (3) is plotted in FIG. 6. From this plot one can see how the roots of the characteristic equation are affected by the change in compensator gain $K_{comp}$. The placement of the two poles due to the hydraulic fluid can be shifted to the left by changing the equivalent damping, $\xi_{eq}$, by increasing the actuator force or moment gain, $K_\alpha$. The real part of the these two poles is $(-\xi_{eq}\omega_h)$. The placement of the zero can be moved to the left by increasing the position feedback gain, Kv. The design objective for the first transfer function, $^yT_{F^{hand}}$, is that the time response due to a step input should have zero or very small amount of overshoot, which can be termed as nonovershooting step response. If this is not satisfied then the actuator acceleration response will go negative for a step change in the force at the hand, $F_{hand}$, and will be perceived by the human operator as acceleration forces at his or her hand that are opposing his or her intended motion.

Achieving a nonovershooting step response is an important feature of the present invention with respect to the single degree-of-freedom system. In order to do so, the pole at the origin must never pass the real part of the two poles caused by the hydraulic fluid. This constraint forces an upper limit on the allowable range of $K_{comp}$. Preferably, the value of $K_{comp}$ should be high. The importance of achieving high $K_{comp}$ gain value is to reduce the affect of plant variation (i.e., change in load, temperature variation, fluid bulk modulus, nonlinear dynamics due to the orifices in the servo valves, etc.). This gain can be increased by adjusting the location of the position feedback gain, Kv, and the actuator force or moment gain, $K_\alpha$. If the hydraulic natural frequency, $\omega_h$, is already high, feeding back the actuator force or moment might then not be necessary. The hydraulic natural frequency, $\omega_h$, can only be adjusted during the mechanical design of the actuator. If $K_{comp}$ still is too low, a classic lag-lead compensator with poles and zeros in between the pole and zeros on the real axis can be utilized and will be limited only by the noise of the sensors and the saturation limits of the drives.

The second transfer function, $^yT_{F_{ext}}$, relates the external contact forces during impact to the actuator velocity. Due to the sign convention of motion (i.e., a positive contact force will generate a negative actuator velocity), the design constraint on this transfer function is that the time response due to a step input of contact force should have zero overshoot or a nonovershooting step response of the actuator velocity. If this is not satisfied then the actuator acceleration will temporarily go positive and the payload will drive into the surface. A small amount of overshoot can be tolerated (base on the acceptability of the operator).

To come close to achieve this objective is basically the same as the previous case with the exception that the numerator of $^yT_{F_{ext}}$ has two zeros that are close to the two poles due to the presence of the hydraulic fluid in the characteristic equation (3) if $K_{comp}$ achieves a high enough value. If $K_{comp}$ is large enough, then the zeros in the numerator of $^yT_{F_{ext}}$ will be almost canceled by the two poles due to the hydraulic fluid in its denominator. In the limit as $K_{comp}$ goes to infinity, $$^yT_{F_{ext}} \to (-1/M)(s+a_v), \text{ when } K_{comp} \to \infty$$

which demonstrates an imperfect pole-zero cancellation. Therefore, in the limit with high gain feedback, the human de-amplifier will feel the mass of the physical object, M, and the programmable viscous friction force.

Figure 7:
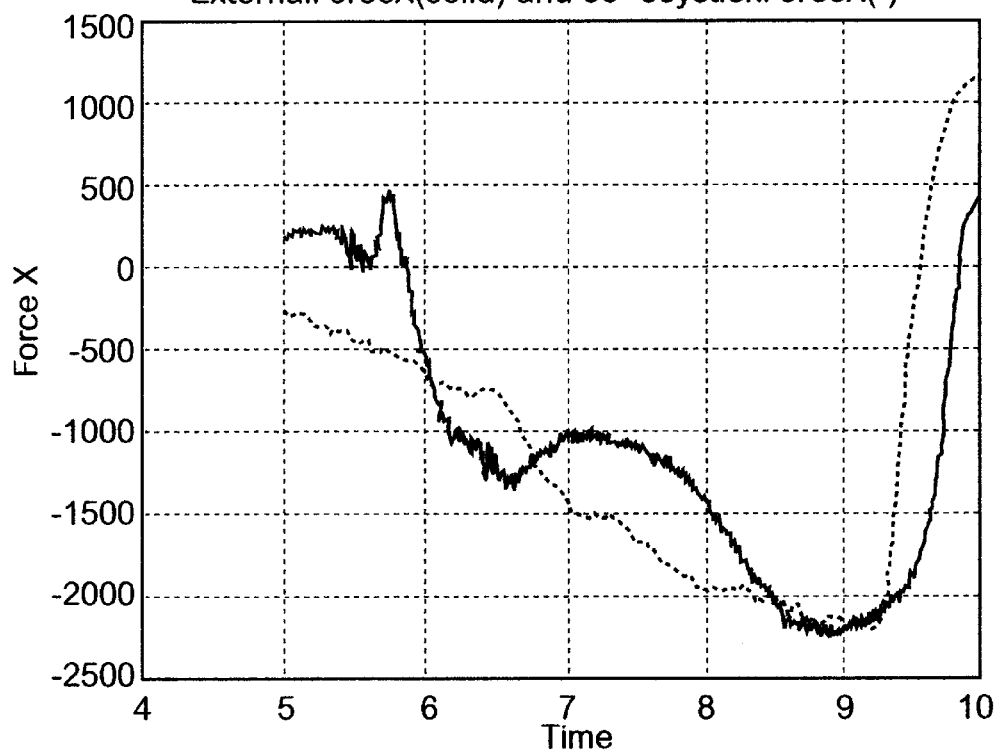
FIG. 7 displays time response during impact with a load (hand force is the dashed line and the external force is the solid line).

FIG. 7 displays time response during impact with a load. The commanded hand or joystick force and the external force in the vertical direction is shown. The force amplification is set at 50. FIG. 7 shows that external force tracks the hand force quite well. This demonstrates that this particular embodiment of the present invention is quite stable and works well, even though the solutions of the characteristic equation (3) obtained through the root locus sketch only approximate the exact solutions of the equation.

Although the present invention has been described with reference to specific details of certain embodiments thereof, it is not intended that such details should be regarded as limitations upon the scope of the invention except as and to the extent that they are included in the accompanying claims. For instance, although the de-amplifier system is presented with force scaling in term of weights, the same principle can be used to provide motion scaling in term of velocity or distance.

What is claimed is:

1. A system for interfacing a human operator and a physical object through a physical plant, wherein the physical plant is driven by at least one actuator and the physical object has dimensions in the range of 1 micrometer to 1 mm, comprising:
   a. means for providing drive signals, comprising:
      i. means for generating incoming signals, wherein the incoming signals include contact force signals representative of forces from the hand of the human operator interacting with the surrounding environment, interacting force signals representative of forces caused at the physical plant by the interaction between the physical plant and the physical object and actuating force signals representative of forces caused at the actuator by the interaction between the physical plant and the physical object;
      ii. means for compensating at least partially the incoming signals directly in response to variations of the environment; and
      iii. means for generating drive signals from the at least partially compensated incoming signals;
   b. means for using the drive signals to manipulate the physical object through the physical plant; and
   c. means for monitoring the motion of the physical object.

2. The system of claim 1, wherein the incoming signal generating means comprises at least one force sensitive device.

3. The system of claim 2, wherein the force sensitive device comprises a sensor selected from the group consisting of a strain gauge type transducer and a semi-conductor based gauge type transducer.

4. The system of claim 1, wherein the providing means further comprises means for receiving and filtering the contact force signals and interacting force signals.

5. The system of claim 4, wherein the receiving and filtering means comprises at least one filter selected from the group consisting of a first order lag filter and a second order lag filter.

6. The system of claim 1, wherein the providing means further comprises means for converting the contact force signals and interacting force signals into an equivalent Cartesian velocity signal vector.

7. The system of claim 1, wherein the providing means further comprises means for converting the contact force signals and interacting force signals into an equivalent force signal vector.

8. The system of claim 1, wherein the providing means further comprises means for integrating the contact force signals and interacting force signals.

9. The system of claim 8, wherein the integrating means comprises an integrator with antiwindup capability.

10. The system of claim 1, wherein the compensating means comprises an inner-feedback loop having a constant gain.

11. The system of claim 10, wherein the inner-feedback loop further comprises a load cell or a clevis pin.

12. The system of claim 10, wherein the inner-feedback loop further comprises an accelerometer.

13. The system of claim 1, wherein the compensating means comprises a compensator for providing a high feedback gain to reduce overshooting to a step response.

14. The system of claim 13, wherein the compensator is capable of producing a constant gain.

15. The system of claim 13, wherein the compensator comprises a series of lag-lead compensators.

16. The system of claim 1, wherein the drive signals generating means comprises a limiter.

17. The system of claim 1, wherein the using means comprises at least one actuator.

18. The system of claim 17, wherein the actuator comprises an actuator selected from the group consisting of a hydraulic actuator and an electric actuator.

19. The system of claim 1, wherein the using means comprises:
   a. a head;
   b. a first arm associated with the head; and
   b. a second arm associated with head,
   the first arm and the second arm are associated with the head in relative positions so that they move toward to each other to hold the physical object and they move away from each other to release the physical object.

20. The system of claim 1, wherein the monitoring means comprises an optical device.

21. The system of claim 20, wherein the optical device comprises at least one optical lens.

22. The system of claim 1, wherein the monitoring means comprises:
   a. a data collector;
   b. a data transmitter; and
   c. a data display.

23. The system of claim 22, wherein the data collector comprises at least one motion sensor.

24. The system of claim 22, wherein the data transmitter comprises a cable.

25. The system of claim 22, wherein the data display comprises a computer screen.

26. The system of claim 22, wherein the data display comprises a TV.

27. A system for interfacing a human operator and a physical object through a physical plant, wherein the physical plant is driven by at least one actuator and the physical object has dimensions in the range of 1 micrometer to 1 mm, comprising:
   a. a controller including:
      i. at least one first force sensitive device for generating contact force signals representative of forces from the hand of the human operator interacting with the surrounding environment;
      ii. at least one second force sensitive device for generating interacting force signals representative of forces caused at the physical plant by the interaction between the physical plant and the physical object;
      iii. at least one third force sensitive device for generating actuating force signals representative of forces caused at the actuator by the interaction between the physical plant and the physical object;
      iv. a compensator for compensating the contact and interacting force signals, wherein the compensator is capable of producing high feedback gain;
      v. an inner-feedback loop having a constant gain for compensating the actuating force signals, the inner-feedback loop comprising a load cell; and
      vi. a limiter receiving the compensated contact force signals, interacting force signals and actuating force signals, and thereby generating drive signals for manipulating the physical object; and
   b. a monitoring device connected to the controller, providing the controller information related to the positions of the physical object, wherein the monitoring device comprises a visual display, whereby the actuator receives the drive signals and uses the drive signals to manipulate the physical object through the physical plant.

28. A method for interfacing a human operator and a physical object through a physical plant, wherein the physical plant is driven by at least one actuator and the physical object has dimensions in the range of 1 micrometer to 1 mm, comprising the steps of:
   a. providing drive signals;
   b. using the drive signals to manipulate the physical object; and
   c. monitoring the motion of the physical object.

29. The method of claim 28, wherein the providing step comprises the steps of:
   a. generating contact force signals representative of forces from the hand of the human operator interacting with the surrounding environment;
   b. generating interacting force signals representative of forces caused at the physical plant by the interaction between the physical plant and the physical object;
   c. generating actuating force signals representative of forces caused at the actuator by the interaction between the physical plant and the physical object;
   d. receiving and filtering the contact force signals and interacting force signals;
   e. compensating the actuating force signals; and
   f. generating drive signals from the contact force signals, interacting force signals and actuating force signals.

30. The method of claim 29, further comprising the steps of:
   a. changing the contact force signals and the interacting force signals into equivalent Cartesian velocity signals;
   b. converting the Cartesian velocity signals into joint velocity signals by inverting a manipulator-specific Jacobian matrix; and
   c. compensating the joint velocity signals with high feedback gain.

31. The method of claim 30, wherein the compensating step comprises the step of solving a characteristic equation of transfer function to determine the gain to reduce overshooting to a step response.

32. The method of claim 29, wherein the actuating force signals compensating step
y=actuator velocitycomprises the step of damping the actuating force signals.

* * * * *